United States Patent [19]

Shionoya et al.

[11] Patent Number: 4,490,362

[45] Date of Patent: Dec. 25, 1984

[54] IMMUNOPOTENTIATOR COMPRISING THE B CHAIN OF RICIN AS AN ACTIVE INGREDIENT

[75] Inventors: Hiroshi Shionoya, Saitama; Hitoshi Takeuchi, Tokyo; Gunki Funatsu, Fukuoka, all of Japan

[73] Assignee: Eisai Co., Ltd., Tokyo, Japan

[21] Appl. No.: 382,364

[22] Filed: May 26, 1982

[30] Foreign Application Priority Data

May 27, 1981 [JP] Japan ................................. 56-79146

[51] Int. Cl.$^3$ ...................... A61K 37/02; A61K 39/00
[52] U.S. Cl. ........................................ 424/177; 424/85
[58] Field of Search ................................. 424/85, 177

[56] References Cited

FOREIGN PATENT DOCUMENTS 0028815 5/1981 European Pat. Off. .

OTHER PUBLICATIONS

Olsnes et al., *Nature*, 249, 627–631, (1974).

*Primary Examiner*—Delbert R. Phillips
*Assistant Examiner*—F. T. Moezie
*Attorney, Agent, or Firm*—Wenderoth, Lind & Ponack

[57] ABSTRACT

An immunopotentiator comprising the B chain of ricin as an active ingredient. The immunopotentiator serves to increase immune response to fungi, viruses and other microorganisms and is therefore effective for prevention or treatment of infectious diseases by such microorganisms.

7 Claims, No Drawings

IMMUNOPOTENTIATOR COMPRISING THE B CHAIN OF RICIN AS AN ACTIVE INGREDIENT

BACKGROUND OF THE INVENTION (1) Field of the Invention:

This invention relates to an immunopotentiator comprising the B chain of ricin as an active ingredient, and more particularly to an immunopotentiator comprising the B chain of ricin as an active ingredient and being effective for prevention and/or treatment of various infectious diseases caused by microorganisms such as fungi or viruses.

(2) Description of the Prior Art:

The term "immunopotentiator" is used to indicate any substance or preparation of substances which exhibits a high degree of potentiation, as its own function, in a humoral or cellular immune response system. An immunopotentiator which, when injected together with an antigen, increases the immune response to the antigen is generally called an "immuno-adjuvant".

The Freund's complete adjuvant, aluminum hydroxide gel and the like have been heretofore used as such immuno-adjuvants. However, they are not applicable to men since they develop intensive inflammatory reactions at injected sites and thus induce swelling, necrosis and/or induration there. The Freund's complete adjuvant is made of killed Mycobacteria, a surfactant and a mineral oil. Thus, it is necessary for the development of its adjuvant activity to convert it together with an aqueous antigen solution or an antigen suspension into a w/o emulsion. Therefore, the Freund's complete adjuvant is accompanied by such drawbacks, that the aforementioned mixing and preparation work is complex and time-consuming and the resultant emulsion is viscous and thick and thus inconvenient for injection.

SUMMARY OF THE INVENTION

With the foregoing in view, the present inventors carried out an intensive study with a view toward finding out a substance which has immunopotentiating activity in both humoral and cellular immune response systems, is free of toxicy such as localized necrosis or induration and can be readily mixed with an antigen and formulated into dosage forms. As a result, it has been unexpectedly found that the B chain of ricin can be used as an adjuvant substance capable of fulfilling the above-described requirements, thereby leading to the completion of this invention.

In one aspect of this invention, there is thus provided an immunopotentiator which comprises the B chain of ricin as an active ingredient.

The immunopotentiator according to this invention, when administered to men and animals, serves to increase immune responses to fungi, viruses and other microorganisms and is therefore effective for prevention or treatment of infectious diseases by such microorganisms as fungi or viruses.

The above and other objects, features and advantages of the present invention will become apparent from the following description and the appended claims.

DETAILED DESCRIPTION OF THE INVENTION AND PREFERRED EMBODIMENTS

The B chain of ricin is a peptide obtained by subjecting ricin, a toxic substance, which has been isolated from the seeds of castor beans, a plant of the Euphorbiaceae, to a reduction treatment and splitting the —S—S— bond of the ricin molecule. The B chain of ricin has a molecular weight of about 33,000 and it has a characteristic chemical feature of binding selectively to galactose.

Ricin per se is a glycoprotein with a molecular weight of about 64,000–65,000 or so. It consists structurally of an A chain having a molecular weight of the order of about 31,000 and a B chain having a molecular weight of the order of about 33,000 connected by a single S—S bond. The A chain functions to inactivate ribosome and to inhibit protein syntheses of cells. In other words, the toxicity or ricin is dependent fully on its A chain. On the other hand, the B chain tends to selectively bind to residual groups of galactose present on the membrane surfaces of eukaryotic animal cells and acts to induce the enclosure of ricin molecules in such cells. The —S—S— bond, which connects the A chain and B chain together, is split when treated with a reducing agent, for example, 2-mercaptoethanol, thereby liberating the A chain and B chain separately. Thus, they can be isolated as separate substances when they are treated suitably, for example, by virtue of affinity chromatography after the reduction.

The thus-isolated B chain of ricin has, as disclosed in literatures which will be referred to later, a similar binding capacity to cells to what it had when it was a constituent of a ricin molecule. Moreover, its toxicity is practically nothing, compared with the toxicity of ricin. When expressing their toxicity in terms of their $LD_{50}$ values on mice, each weighing 25 g, after the lapse of 72 hours from intraperitoneal administration, the safety of the chain B of ricin will be easily appreciated because $LD_{50}$ of ricin is as little as 0.1 μg/mouse while that of the B chain is as much as 10 μg/mouse or more. Accordingly, no necrosis will be induced even if the B chain of ricin is injected locally.

Prior art literatures will be enumerated below to show the state of the art as to ricin, and its A chain and B chain:

Funatsu, G., et al, Agric. Biol. Chem. 43, 2221(1979); and

Olsnes, S., et al, Nature 249, 627(1974).

It has been found by the present inventors that, as shown by Experiments to be described later, the B chain of ricin has an immunopotentiating effect in both humoral and cellular immune response systems. This finding is novel and cannot be readily inferred from the prior art knowledge. As a matter of fact, it has been known that the immune system in vertebrates consists of two basic immune systems against infections and cancer cells. One is the cellular immune response system effective mainly against infections by fungi, viruses, intracellular parasitic bacteria, etc. and the other is the humoral immune response system effective for defence mainly against infections by viruses and extracellular parasitic bacteria.

From the above-mentioned finding and prior art knowledge, it is readily envisaged that the immunopotentiator according to this invention is, when administered to men and animals, capable of enhancing the immune response to fungi, viruses, and other microorganisms, and thus effective for prevention and treatment of infectious diseases by microorganisms such as fungi or viruses.

The minimum dosage of the B chain of ricin in the immunopotentiator according to this invention, which dosage shows an immunopotentiating activity, is 1 ng per human or animal irrespective of body. Its maximum dosage is 500 μg/kg.

Since the B chain of ricin is soluble in water, the immunopotentiator according to this invention can be provided as an aqueous solution. This permits one to mix the immunopotentiator according to this invention with an antigen and vaccine and to immunologically administer them in the form of a unit dosage. In this case, they may be administered subcutaneously, intramuscularly, intraperitoneally or intrapleurally. Needless to say, the immunopotentiator according to this invention may also be administered separately from an antigen and vaccine, and in this case, apart from the aforementioned administration routes, it may be administered intravenously or intratumorally. It is sufficient to administer the immunopotentiator according to this invention twice a week to once in two weeks.

A particularly preferred dosage form of the immunopotentiator according to this invention is an injectable preparation. For instance, it may be formulated into an injectable ampoule containing 0.1 to 1 ml of a physiological saline or a neutral to weakly acidic buffer which in turn contains the B chain of ricin in a concentration of 10 ng to 100 mg/ml. Alternatively, it may be formed into a lyophilized ampoule if necessary. Furthermore, it is optional to incorporate galactose in a preparation in order to make a concentration of 1 mM to 100 mM bcause the B chain of ricin is known to maintain its activity stably in the presence of galactose. The present inventors also investigated the possibility of adding lactose to the B chain of ricin. As a result, it was found that lactose has, similar to galactose, a stabilizing effect. Accordingly, it is feasible to incorporate lactose or lactose and galactose in the preparation, instead of galactose. They may thus be contained as parts of additives in the immunopotentiator according to this invention. By the way, the injectable preparation of the immunopotentiator according to this invention may be formulated by any commonly known formulation method of injectable preparations.

The immunopotentiating activity of the B chain of ricin will be illustrated by the following Experiments.

EXPERIMENT 1

Samples

Eight (8) samples, numbered as Nos. 1 through 8 respectively, of different compositions as shown in Table 1.

TABLE 1

| Ingredient | Sample No. | | | | | | | |
|---|---|---|---|---|---|---|---|---|
| | 1 | 2 | 3 | 4 | 5 | 6 | 7 | 8 |
| BSA (μg) | 10 | 10 | 10 | 10 | 10 | 10 | 10 | 10 |
| The B chain of ricin (ng) | 0 | 1 | 10 | 100 | 1000 | 1 | 10 | 100 |
| Galactose (mM) | 0 | 0 | 0 | 0 | 0 | 10 | 10 | 10 |
| PS (ml) | 0.1 | 0.1 | 0.1 | 0.1 | 0.1 | 0.1 | 0.1 | 0.1 |

(Note)
BSA: Bovine serum albumin
PS: Injectable physiological saline

Procedure

Each sample was injected subcutaneously into the backs of mice (female $CDF_1$) having a body weight of 20 to 23 g, and 14 days later, the mice were treated with injection in the same way as above to induce secondary immunization. For each sample, were employed 6 mice as a group. Then, humoral immunity (A) and cellular immunity (B) were determined with respect to the mice, which had been subjected to secondary immunization, in the following manner:

(A) Determination of humoral immunity

Blood was collected in an amount of 0.1 ml from the retroorbital plexus of each mouse on day 21. After adding the thus-collected blood to 0.2 ml of a physiological saline containing 5 units of heparin and mixing them, the resultant mixture was subjected to centrifugal separation. The supernatant was then collected and stored at −20° C. The plasma was diluted by 5 times the original plasma. The anti-BSA antibody titer of each mouse blood was measured in accordance with the hemmagglutination method of tanned sheep red blood cells passively sensitized with BSA [PROTEINS, NUCLEIC ACIDS, ENZYMES; separate print "IMMUNOBIOCHEMISTRY", Vol. 11, No. 15, 1506 (1966) in Japanese].

(B) Determination of cellular immunity

In accordance with the method of Robinson, et al. [Robinson, J. H., Scand. J. Immunol., 5, 299 (1976)], 10 μl of a physiological saline containing 10 μg of BSA was injected subcutaneously into an auricle of each mouse (challenge) on day 21 and 24 hours later, the increment in thickness of the auricle was measured.

Results

Results of the humoral immunity determination and cellular immunity determination are shown, respectively, in Tables 2 and 3.

TABLE 2

| Sample No. | BSA-sensitized hemagglutinin value (plasma dilution multiple ± S.E.*) | Significance against control** (P) |
|---|---|---|
| 1 | $2^{2.0 \pm 0.4} \times 10$ | |
| 2 | $2^{2.2 \pm 0.5} \times 10$ | |
| 3 | $2^{4.0 \pm 0.6} \times 10$ | <0.01 |
| 4 | $2^{5.0 \pm 0.3} \times 10$ | <0.01 |
| 5 | $2^{5.8 \pm 0.2}$ | <0.01 |
| 6 | $2^{2.8 \pm 0.5} \times 10$ | <0.1 |
| 7 | $2^{4.0 \pm 0.4} \times 10$ | <0.01 |
| 8 | $2^{4.7 \pm 0.3} \times 10$ | <0.01 |

(Note)
*S.E. = standard error
**Calculated by Student's t test

TABLE 3

| Sample No. | Increment in thickness of auricle ($10^{-3}$ cm ± S.E.*) | Significance against control** (P) |
|---|---|---|
| 1 | 5.7 ± 1.2 | |
| 2 | 5.0 ± 0.7 | |
| 3 | 13.7 ± 2.2 | <0.01 |
| 4 | 17.7 ± 1.4 | <0.01 |
| 5 | 28.6 ± 2.2 | <0.01 |
| 6 | 7.8 ± 1.7 | <0.1 |
| 7 | 12.8 ± 1.4 | <0.01 |
| 8 | 14.5 ± 2.2 | <0.01 |

(Note)
*S.E. = standard error
**Calculated by Student's t test

From Tables 2 and 3, it is appreciated that the B chain of ricin, when used 1 ng or more, exhibits immunopotentiating activities in both hemoral and cellular immune response systems against BSA. Its effectiveness will not be deleteriously affected by an addition of galactose.

EXPERIMENT 2

Samples

Six (6) samples, numbered as Nos. 1 through 6 respectively, of different compositions as shown in Table 4.

TABLE 4

| Ingredient | Sample No. | | | | | |
|---|---|---|---|---|---|---|
|  | 1 | 2 | 3 | 4 | 5 | 6 |
| Radio-inactivated Meth-A cancer cells | $1 \times 10^5$ | $1 \times 10^5$ | $1 \times 10^5$ | $1 \times 10^5$ | $1 \times 10^5$ | $1 \times 10^5$ |
| The B chain of ricin (ng) | 0 | 0.1 | 1 | 10 | 1 | 1 |
| Lactose (mM) | 0 | 0 | 0 | 0 | 100 | 0 |
| Galactose (mM) | 0 | 0 | 0 | 0 | 0 | 10 |
| MEM Culture medium (ml) | 0.1 | 0.1 | 0.1 | 0.1 | 0.1 | 0.1 |

Meth-A cancer cells were serially transplanted from the abdominal cavity of one Balb/c mouse to that of another Balb/c mouse. After a week of the transplantation of Meth-A cancer cells, ascites was collected. The Meth-A cancer cells were then washed with Eagle's MEM culture medium. The term "Radio-inactivated Meth-A cancer cells", which appears in Table 4, means Meth-A cancer cells which had been inactivated by a radiation of 9000 R using cobalt-60 as a radiation source.

Procedure

Each sample was subcutaneously injected into the left side of the dorsum of each female Balb/c mouse having a body weight of 20 to 23 g to immunize the mouse. For each sample, were employed 6 mice as a group. Then, the thus-immunized mice were subjected to determination of immunity against tumors in the following manner.

Namely, two weeks after the immunization, $1 \times 10^6$ Meth-A cancer cells were transplanted subcutaneously at the right side of the dorsum of each mouse. After the lapse of further 3 weeks, a grown tumor was removed and its weight was measured.

Results

Results are tabulated in Table 5.

TABLE 5

| Sample No. | Weight of tumor (g ± S.E.*) | Significance against control** (P) |
|---|---|---|
| 1 | 0.76 ± 0.21 |  |
| 2 | 0.55 ± 0.20 |  |
| 3 | 0.10 ± 0.05 | <0.02 |
| 4 | 0.08 ± 0.04 | <0.01 |
| 5 | 0.18 ± 0.18 | <0.05 |
| 6 | 0.10 ± 0.10 | <0.02 |

(Note)
*S.E. = standard error
**Calculated by Student's t test

It is realized from Table 5 that the B chain of ricin, when used in an amount of 1 ng or more, exhibits a distinct antitumor immunopotentiating effect. Its effectiveness is not affected by an addition of lactose or galactose.

The present invention will be illustrated further in detail by the following examples.

EXAMPLE 1

Nine milliliters of a 0.01M phosphate buffer(pH 6.0) containing 0.01M of galactose and 0.15M of sodium chloride were mixed with 1 ml of a saturated ammonium sulfate suspension containing 10 mg of the B chain of ricin. The resultant mixture was centrifuged for 20 minutes at 10,000 rpm. The supernatant was filtered through a 0.45 μm filter to remove any microorganisms. The filtrate was then put into a sterilized cellophane tube and dialyzed against 5 liters of the same buffer. The dialyzate was drawn out of the cellophane tube under sterile conditions and diluted by 10 times with sterilized buffer of the same type as used above so as to adjust the concentration of the B chain of ricin to 100 μ/ml. The thus-obtained solution was filled in 1 ml ampoules and hermetically sealed therein.

EXAMPLE 2

The procedure of EXAMPLE 1 was followed except that the dialyzate was diluted by 100 times with the same buffer to adjust the concentration of the B chain of ricin to 10 μg/ml.

EXAMPLE 3

The procedure of EXAMPLE 1 was repeated except that the dialyzate was diluted by 1000 times with the same buffer to adjust the concentration of the B chain of ricin to 1 μg/ml.

EXAMPLE 4

The procedure of EXAMPLE 1 was followed except that the final solution was placed in vial tubes, each having an internal volume of 10 ml, and then lyophilized, instead of filling it in 1 ml ampoules and hermetically sealing it therein.

EXAMPLE 5

The procedure of EXAMPLE 1 was repeated except for the adoption of a 0.01M phosphate buffer containing 0.1M of lactose and 0.15M of sodium chloride in place of the 0.01M phosphate buffer containing 0.01M of galactose and 0.15M of sodium chloride.

EXAMPLE 6

The procedure of EXAMPLE 1 was followed except for the adoption of 0.01M phosphate buffer containing 0.1M of lactose, 0.01M of galactose and 0.15M of sodium chloride in lieu of the 0.01M phosphate buffer containing 0.01M of galactose and 0.15M of sodium chloride.

Having now fully described the invention, it will be apparent to one of ordinary skill in the art that many changes and modifications can be made thereto without departing from the spirit or scope of the invention as set forth herein.

What is claimed is:

1. An aqueous immunopotentiator composition comprising the B chain of ricin in an aqueous solution, said aqueous composition being in an injectable dosage form, and wherein the B chain of ricin is present in said aqueous composition in a concentration of 10 ng to 100 mg/ml.

2. The aqueous composition of claim 1 wherein the composition further comprises a stabilizing amount, to maintain the immunoactivity of the B chain ricin in solution, of lactose or a mixture of lactose and galactose.

3. A method for treating a patient with an immunopotentiator to increase the immunopotentiating effects against diseases both in humoral and cellular immune response systems, which comprises administering to the patient from 1 ng to 500 µg/kg of the B-chain of ricin.

4. A method according to claim 3 wherein the disease is a virus.

5. A method according to claim 3 wherein the disease is a fungus.

6. An immunopotentiating composition comprising B-chain ricin as the immunopotentiator in a concentration of from 10 ng to 100 mg and a pharmaceutically acceptable liquid carrier.

7. The composition of claim 6 which further comprises lactose or lactase and galactose as an additive.

* * * * *